United States Patent
Welsh et al.

(10) Patent No.: US 12,414,759 B2
(45) Date of Patent: Sep. 16, 2025

(54) METHOD AND SYSTEM FOR AUTOMATIC 3D-FMBV MEASUREMENTS

(71) Applicant: NewSouth Innovations Pty Limited, New South Wales (AU)

(72) Inventors: Alec Welsh, New South Wales (AU); Gordon Stevenson, New South Wales (AU)

(73) Assignee: NewSouth Innovations Pty Limited, New South Wales (AU)

( * ) Notice: Subject to any disclaimer, the term of this patent is extended or adjusted under 35 U.S.C. 154(b) by 243 days.

(21) Appl. No.: 17/906,732

(22) PCT Filed: Mar. 19, 2021

(86) PCT No.: PCT/AU2021/050249
§ 371 (c)(1),
(2) Date: Sep. 19, 2022

(87) PCT Pub. No.: WO2021/184075
PCT Pub. Date: Sep. 23, 2021

(65) Prior Publication Data
US 2023/0148147 A1    May 11, 2023

(30) Foreign Application Priority Data
Mar. 19, 2020  (AU) ............................ 2020900837

(51) Int. Cl.
*G06T 7/00* (2017.01)
*A61B 8/00* (2006.01)
(Continued)

(52) U.S. Cl.
CPC ............... *A61B 8/06* (2013.01); *A61B 8/466* (2013.01); *A61B 8/488* (2013.01); *A61B 8/5223* (2013.01);
(Continued)

(58) Field of Classification Search
CPC .......... A61B 8/06; A61B 8/466; A61B 8/488; A61B 8/5223; A61B 8/5284; A61B 8/483;
(Continued)

(56) References Cited

U.S. PATENT DOCUMENTS 5,353,220 A   10/1994  Ito et al.
5,840,034 A   11/1998  Amemiya et al.
(Continued)

FOREIGN PATENT DOCUMENTS

WO    WO 2021/184075 A1    9/2021

OTHER PUBLICATIONS

Welsh et al., "Three-dimensional US Fractional Moving Blood Volume: Validation of Renal Perfusion Quantification", Radiology, 293:460-468 (2019) (Year: 2019).*
(Continued)

*Primary Examiner* — Van D Huynh
(74) *Attorney, Agent, or Firm* — Knobbe, Martens, Olson & Bear, LLP

(57) ABSTRACT

A method of quantifying a 3D fractional moving blood volume (3D-FMBV) in a tissue volume of a subject using an ultrasound system, including acquiring images of the tissue volume from a power doppler scan of the tissue volume; applying image enhancement settings to the images; segmenting an organ, tissue or region thereof from the image data; determining geometric partitions of the segments based on distance from the transducer head of the ultrasound system; and computing a 3D-FMBV using a 3D-FMBV analysis algorithm from the partitions.

20 Claims, 5 Drawing Sheets

(51) Int. Cl.
| | |
|---|---|
| *A61B 8/06* | (2006.01) |
| *G01S 7/52* | (2006.01) |
| *G06T 5/00* | (2006.01) |
| *G06T 7/11* | (2017.01) |

(52) U.S. Cl.
CPC ........ *A61B 8/5284* (2013.01); *G01S 7/52068* (2013.01); *G06T 5/00* (2013.01); *G06T 7/11* (2017.01); *G06T 2207/10136* (2013.01); *G06T 2207/20081* (2013.01); *G06T 2207/20084* (2013.01); *G06T 2207/30104* (2013.01)

(58) Field of Classification Search
CPC ..... A61B 5/026; A61B 5/7267; A61B 5/0285; G01S 7/52068; G01S 7/52038; G01S 15/8988; G01S 15/8993; G01S 15/582; G01S 15/8906; G01S 15/8979; G06T 5/00; G06T 7/11; G06T 2207/10136; G06T 2207/20081; G06T 2207/20084; G06T 2207/30104; G06T 2207/10016; G06T 2207/10132; G06T 7/0012; G06T 7/62; G06T 11/003; G06T 2207/20172; G06N 3/045; G06N 3/08
See application file for complete search history.

(56) References Cited

U.S. PATENT DOCUMENTS

| | | | |
|---|---|---|---|
| 5,860,929 A * | 1/1999 | Rubin ................... | A61B 8/463 600/454 |
| 6,186,948 B1 | 2/2001 | Kamiyama et al. | |
| 6,511,426 B1 | 1/2003 | Hossack et al. | |
| 2004/0138560 A1* | 7/2004 | Paladini ............. | G01S 7/52044 600/437 |
| 2005/0251039 A1* | 11/2005 | Chalana ............. | G01S 15/8993 600/437 |
| 2006/0241461 A1* | 10/2006 | White ...................... | A61B 8/06 600/454 |
| 2006/0241463 A1* | 10/2006 | Shau ........................ | A61B 8/08 600/455 |
| 2009/0148018 A1* | 6/2009 | Averkiou ............. | A61B 8/0883 382/131 |
| 2011/0144495 A1* | 6/2011 | Wilkening ............ | A61B 8/483 600/443 |
| 2014/0160114 A1 | 6/2014 | Stevenson et al. | |
| 2016/0007970 A1* | 1/2016 | Dufour ................ | A61B 8/5207 600/437 |
| 2018/0279996 A1 | 10/2018 | Cox et al. | |
| 2019/0142386 A1 | 5/2019 | Srinivasan et al. | |
| 2019/0365650 A1 | 12/2019 | Nagy et al. | |
| 2019/0380684 A1* | 12/2019 | Insana ................... | A61B 8/5207 |
| 2020/0051257 A1* | 2/2020 | Sauer ...................... | G06T 7/344 |

OTHER PUBLICATIONS

Yin et al., "Standardization of blood flow measurements by automated vascular analysis from power Doppler ultrasound scan," Proc. SPIE 11314, Medical Imaging 2020: Computer-Aided Diagnosis, 113144C (Mar. 16, 2020); https://doi.org/10.1117/12.2549349 (Year: 2020).*
Stevenson et al., "A Technique for the Estimation of Fractional Moving Blood vol. by Using Three-dimensional Power Doppler US", Radiology, in 7 pages (2014) (Year: 2014).*
Welsh et al., "Three-dimensional US Fractional Moving Blood vol. Validation of Renal Perfusion Quantification", Radiology, 293:460-468 (2019) (Year: 2019).*
Collins et al., "Influence of power Doppler gain setting on Virtual Organ Computer-aided AnaLysis indices in vivo: can use of the individual sub-noise gain level optimize information?", Ultrasound Obstet Gynecol 40:75-80 (2012).
Diniz et al., "Deep Learning Strategies for Ultrasound in Pregnancy", EMJ Reproductive Health, 6(1):73-80 (2020).
Hu et al., "Automated Placenta Segmentation with a Convolutional Neural Network Weighted by Acoustic Shadow Detection", IEEE, pp. 6718-6723 (2019).
International Search Report and Written Opinion issued in International Application No. PCT/AU2021/050249, mailed on May 26, 2021.
Stevenson et al., "A Technique for the Estimation of Fractional Moving Blood Volume by Using Three-dimensional Power Doppler US", Radiology, in 7 pages (2014).
Welsh et al., "Three-dimensional US Fractional Moving Blood Colume: Validation of Renal Perfusion Quantification", Radiology, 293:460-468 (2019).
Yin et al., "Standardization of blood flow measurements by automated vascular analysis from power Doppler ultrasound scan", Proc SPIE Int. Soc. Opt. Eng., Author Manuscript, pp. 1-4 (2020).
Extended European Search Report issued in EP Application No. 21770909.6, dated Apr. 26, 2024.
Yu et al., "Assessment of Placental Fractional Moving Blood vol. Using Quantitative Three-Dimensional Power Doppler Ultrasound", Ultrasound in Med. & Biol., 2003, 29(1): 19-23.
Avnet et al., "Developing a SIMULINK mathematical model to simulate the fetal cardiovascular system (CVS)." Ultrasound in Obstetrics and Gynecology, 2018, 52(1), in 3 pages.
Cheung et al., "Feasibility of image registration and fusion for evaluation of structure and perfusion of the entire second trimester placenta by three-dimensional power Doppler ultrasound." Placenta, 2020, 94: 13-19.
Clark et al., "Understanding abnormal uterine artery Doppler waveforms: A novel computational model to explore potential causes within the utero-placental vasculature." Placenta, 2018, 66: 74-81.
Gu et al., "Applying spatial-temporal image correlation to the fetal kidney: Repeatability of 3D segmentation and volumetric impedance indices." AJUM, 2018, 21(3): 169-178.
International Search Report issued in International Application No. PCT/AU2022/050787, mailed on Sep. 20, 2022.
Lobo et al., "Four-Dimensional Ultrasound for Evaluating Newborn Cardiac Output: A Pilot Study of Healthy Infants." Neonatology, 2019, 116: 115-122.
Looney et al., "Fully Automated 3-D Ultrasound Segmentation of the Placenta, Amniotic Fluid, and Fetus for Early Pregnancy Assessment." IEEE Transactions On Ultrasonics, Ferroelectrics, and Frequency Control, 2021, 68(6): 2038-2047.
Looney et al., "Fully automated, real-time 3D ultrasound segmentation to estimate first trimester placental volume using deep learning." JCI insight, 2018, pp. 1-9.
Looney et al., "3D ultrasound file reading and coordinate transformations." Journal of Open Source Software, 2019, 1 page.
Martinoli et al., "Gain Setting in Power Doppler US." Radiology, 1997, 1 page.
Rubin et al., "Power Doppler US: A Potentially Useful Alternative to Mean Frequency-based Color Doppler US." Radiology, 1994, 190: 853-856.
Sanderson et al., "Selection of the Sub-Noise Gain Level for Acquisition of Vocal Data Sets: A Reliability Study." Ultrasound in Med. & Biol., 2014, 40(3): 562-567.
Stevenson et al., "Automated Visualization and Quantification of Spiral Artery Blood Flow Entering the First-Trimester Placenta, Using 3-D Power Doppler Ultrasound." Ultrasound in Med. & Biol., 2018, 44(3): 522-531.
Weerasinghe et al., "Multi-parametric Fusion of 3D Power Doppler Ultrasound for Fetal Kidney Segmentation using Fully Convolutional Neural Networks." IEEE Journal of Medical and Health Informatics, 2020, pp. 1-8.

* cited by examiner

METHOD AND SYSTEM FOR AUTOMATIC 3D-FMBV MEASUREMENTS

TECHNICAL FIELD

The technology relates to a method and system to automatically calculate 3D-FMBV (Fractional Moving Blood Volume) from three-dimensional and four-dimensional ultrasound volumes received from a conventional power Doppler ultrasound imaging system.

CROSS REFERENCE TO RELATED APPLICATION

This application claims priority to Australian provisional patent application number 2020900837 filed 19 Mar. 2020, which is incorporated by cross-reference in its entirety.

BACKGROUND

Ultrasound is an imaging modality used across medicine for diagnosis and monitoring of disease and pathology. It is favoured as a non-invasive, inexpensive bedside tool that can provide images (using B-Mode or grey-scale) of organs and structures and is the most widely used medical image modality used worldwide. When frequency changes (Doppler ultrasound) are incorporated into structural imaging (B-mode ultrasound) it may additionally be used to evaluate blood flow. Changes in the frequency of the ultrasound echo relative to that of insonation can give movement information about interrogated objects; most frequently these are red blood cells within blood vessels.

The most common form of Doppler imaging shows the velocity of the blood flow within a large vessel creating a display of this waveform as 'Pulsed Wave' Doppler (showing changes in velocity of scatterers). Alternatively, a 'Colour Flow Mapping or Colour Doppler' image may be displayed where the velocity change is superimposed upon the grey-scale image for measurement.

An alternate form of colour flow mapping shows the integral of the frequency spectrum or phase shifts which correlates to the number of moving scatters. This is known as 'Power' Doppler ultrasound. It is favoured in some situations as it is independent of the angle of insonation and is able to show the amplitude of very low frequency Doppler changes; though it lacks information relating to the ultrasound frequency change and therefore velocity of movement. Power Doppler refers to the summation of the Doppler spectrum and has been proposed in multiple studies as representative of perfusion/vascularity of tissue.

An index called Fractional Moving Blood Volume (FMBV) integrates the amplitude of the Doppler frequency shift within a given two-dimensional (2D) area, to standardize this against the potential maximum at that depth of insonation (scanning) and thus generate a percentage value. Without that standardisation, machine settings and loss of signal with depth of scanning (known as attenuation) influence the measured vascularity/perfusion. Two-dimensional ultrasound imaging is generated by the ultrasound transducer scanning in a single plane across an area of tissue and 'interrogating' individual vertical scan lines to receive echoes from differing depths. These multiple lines are then summated to create a two-dimensional image of the tissue or area of insonation beneath the ultrasound transducer.

Three-dimensional ultrasound imaging may be generated by a number of techniques. The most common involves a larger ultrasound transducer internally sweeping its 2D transducer head across an area of tissue by stepwise motor. This results in a number of two-dimensional ultrasound images being combined into a three-dimensional block of tissue. This potentially allows interrogation of a whole area or organ rather than a single slice or plane of tissue.

Four-dimensional ultrasound imaging relates to quick acquisition of three-dimensional ultrasound volumes, resulting in a number of ultrasound volumes representing different phases of the cardiac cycle. Individual ultrasound frames that are judged to represent a particular phase of the cardiac cycle are selected using either greyscale or Doppler changes. Each of the frames perceived to relate to the same phase of the cardiac cycle are reconstructed into a volume, such that there are multiple three-dimensional volumes, each with frames synchronized to the same phase of the cardiac cycle. This potentially allows interrogation of the changes in vascularity within the cardiac cycle to be used to estimate the resistance to blood flow or vascular impedance.

The present inventors have developed a method and system to automatically calculate 3D or 4D-FMBV and, optionally impedance to flow from three-dimensional and four dimensional ultrasound volumes received from a conventional power Doppler imaging system.

SUMMARY

In a first aspect, there is provided a method of quantifying a 3D fractional moving blood volume (3D-FMBV) in a tissue volume of a subject using an ultrasound system, comprising:
 (a) acquiring images of the tissue volume from a power Doppler scan of the tissue volume;
 (b) applying image enhancement settings to the images;
 (c) segmenting an organ, tissue or region thereof from the image data;
 (d) determining geometric partitions of the segments based on distance from the transducer head of the ultrasound system; and
 (e) computing a 3D-FMBV using a 3D-FMBV analysis algorithm from the partitions.

In one embodiment the segmenting uses a neural network trained to identify an organ or tissue.

The partitions may be determined from their membership to the region from the neural network output and their Euclidean distance from the transducer head.

The image enhancement settings are selected from wall motion, overall gain, power Doppler gain, pulse repetition filter, line density, gain compensation, lateral gain compensation, dynamic range, and frequency.

In some embodiments the image enhancement settings are automatically applied to the images.

The neural network may be trained on a combination of power Doppler and greyscale imaging. The neural network is a fully convolutional neural network for example having an encoder-decoder style architecture such as U-Net, V-Net, or U-Net++.

In one embodiment the 3D-FMBV analysis algorithm comprises
 (a) identifying, in a reference portion of each partition, a reference Doppler power level associated with 100% flow;
 (b) computing a mean power estimate equal to the sum of respective target Doppler power levels of a plurality voxels within the partition divided by the number of the plurality voxels within the partition;

(c) computing, for each partition, a fractional moving blood volume estimate by normalizing the mean power to the reference Doppler power level; and (d) ensembling the fractional moving blood volume estimates to determine the 3D-FMBV for an organ, tissue or region thereof.

In some embodiments the images are acquired in synchronisation with the cardiac cycle of the subject. In these embodiments images that represent a particular phase of the cardiac cycle are selected and a 4D-FMBV is computed using the 3D-FMBV analysis algorithm for each of the selected images.

The method may further comprise generating a visual display of the 3D-FMBV or the 4D-FMBV.

In a second aspect there is provided an ultrasound system comprising a processor adapted to receive log compression data from a signal processor, and a program storage device readable by the processor and embodying a program of instructions executable by the processor to perform the method of the first aspect.

Definitions

Throughout this specification, unless the context clearly requires otherwise, the word "comprise", or variations such as "comprises" or "comprising", will be understood to imply the inclusion of a stated element, integer or step, or group of elements, integers or steps, but not the exclusion of any other element, integer or step, or group of elements, integers or steps.

Throughout this specification, the term 'consisting of' means consisting only of.

The term 'consisting essentially of' means the inclusion of the stated element(s), integer(s) or step(s), but other element(s), integer(s) or step(s) that do not materially alter or contribute to the working of the invention may also be included.

Any discussion of documents, acts, materials, devices, articles or the like which has been included in the present specification is solely for the purpose of providing a context for the present technology. It is not to be taken as an admission that any or all of these matters form part of the prior art base or were common general knowledge in the field relevant to the present technology as it existed before the priority date of each claim of this specification.

Unless the context requires otherwise or specifically stated to the contrary, integers, steps, or elements of the technology recited herein as singular integers, steps or elements clearly encompass both singular and plural forms of the recited integers, steps or elements.

In the context of the present specification the terms 'a' and 'an' are used to refer to one or more than one (i.e., at least one) of the grammatical object of the article. By way of example, reference to 'an element' means one element, or more than one element.

In the context of the present specification the term 'about' means that reference to a figure or value is not to be taken as an absolute figure or value, but includes margins of variation above or below the figure or value in line with what a skilled person would understand according to the art, including within typical margins of error or instrument limitation. In other words, use of the term 'about' is understood to refer to a range or approximation that a person or skilled in the art would consider to be equivalent to a recited value in the context of achieving the same function or result.

As used herein, the term 'image' broadly refers to both viewable images and data representing a viewable image. However, many embodiments generate (or are configured to generate) at least one viewable image. In addition, as used herein, the term 'image' is used to refer to an ultrasound mode such as B-mode, CF-mode and/or sub-modes of CF such as power Doppler (PD), tissue velocity imaging (TVI), Angio, B-flow, BMI, BMI Angio, and in some cases also MM, CM, pulsed wave (PW), tissue velocity doppler (TVD), continuous wave (CW) where the 'image' and/or 'plane' includes a single beam or multiple beams.

Furthermore, the term processor or processing unit, as used herein, refers to any type of processing unit that can carry out the required calculations needed for the invention, such as single or multi-core: CPU, GPU, digital signal processor, field-programmable gate array, application-specific integrated circuit, or a combination thereof.

It is to be noted that various embodiments herein the generation or formation of images may include processing for forming images that in some embodiments includes beamforming and in other embodiments does not include beamforming. For example, an image can be formed without beamforming, such as by multiplying the matrix of demodulated data by a matrix of coefficients so that the product is the image, and wherein the process does not form any beams.

In various embodiments, ultrasound processing to form images is performed, including automated machine settings (gain etc), for example, in software, firmware, hardware, or a combination thereof. One implementation of an ultrasound system in accordance with various embodiments is illustrated in FIG. 1.

Those skilled in the art will appreciate that the technology described herein is susceptible to variations and modifications other than those specifically described. It is to be understood that the technology includes all such variations and modifications. For the avoidance of doubt, the technology also includes all of the steps, features, and compounds referred to or indicated in this specification, individually or collectively, and any and all combinations of any two or more of said steps, features and compounds.

In order that the present technology may be more clearly understood, preferred embodiments will be described with reference to the following drawings and examples.

trained on 3D B-Mode data (blue; bottom-middle) and finally, with 3D-US and PD data as inputs to the CNN (green; bottom-right).

Figure 4:
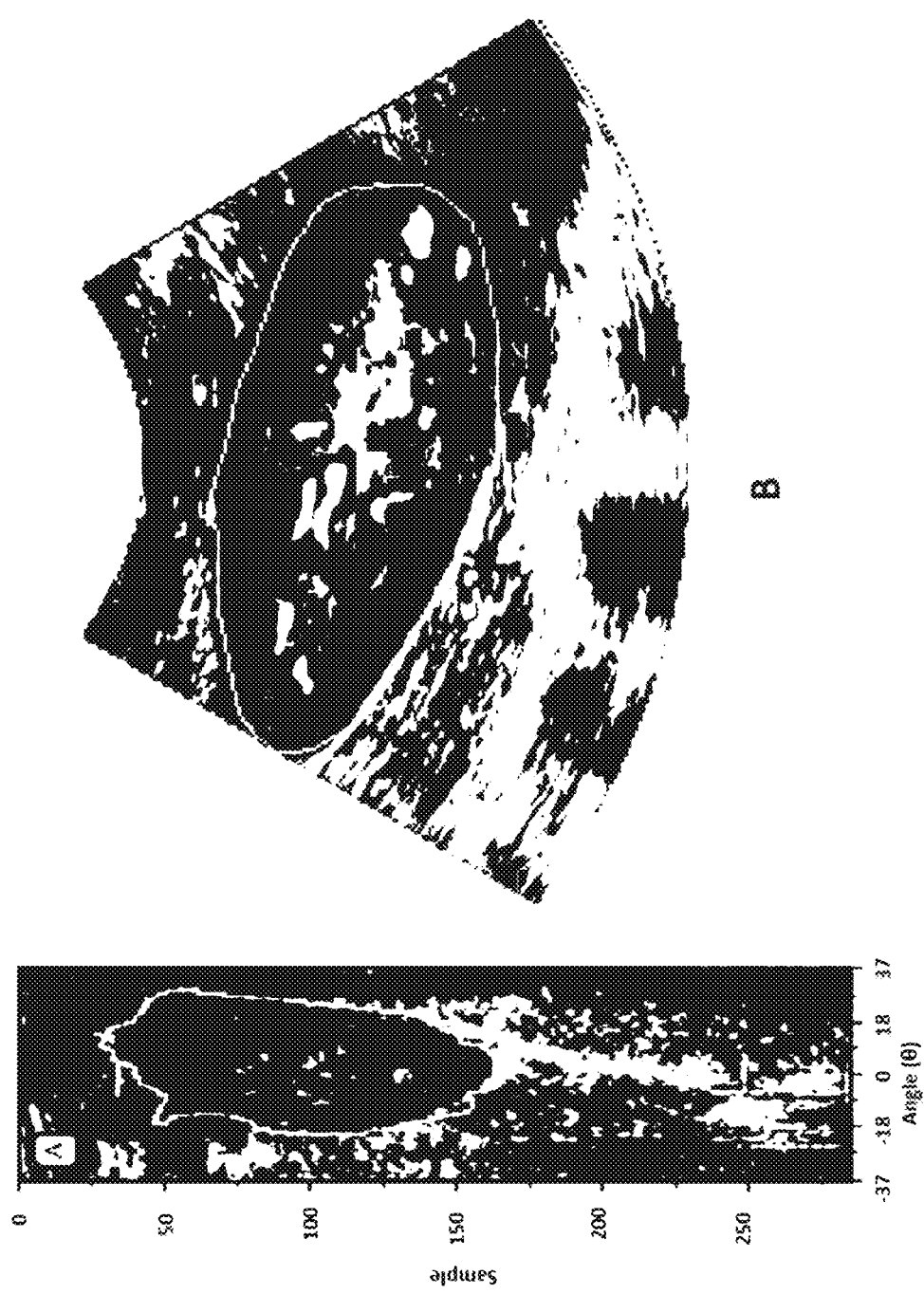
Figure 5:
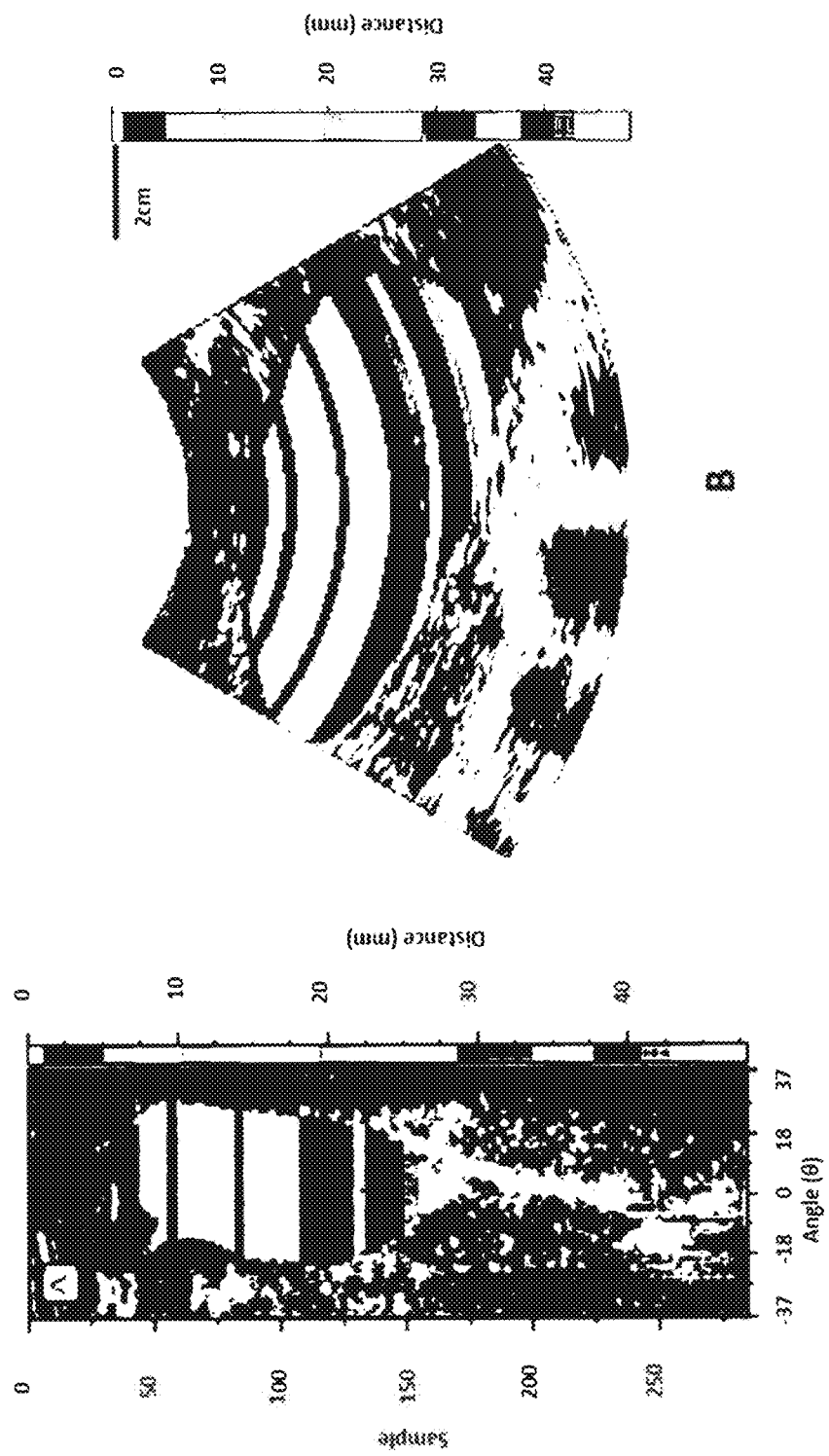

FIG. 4 (A) illustrates a two-dimensional image of a three-dimensional power Doppler data shown in the scanline (toroidal) space and (B) a two dimensional image of a three dimensional power Doppler data shown in the Cartesian or display space;

FIG. 5 (A) illustrates a sampled version of FIG. 4 (A), where the data in the organ mask is partitioned according to the voxels' distance from the transducer head; and (B) depicts a forward transformed image from FIG. 5 (A).

DESCRIPTION OF EMBODIMENTS

Illustrative embodiments of the invention are described below as it might be employed in the method of estimating the fractional moving blood volume with power Doppler ultrasound. Not all features of an actual implementation are described and it will be appreciated that in the development of any such actual embodiment numerous implementation-specific decisions must be made to achieve the developers' specific goals, such as compliance with system-related constraints, which will vary from one implementation to another. Moreover, it will be appreciated that such a development effort might be complex and time-consuming, but would nevertheless be a routine undertaking for those of ordinary skill having the benefit of this disclosure.

Ultrasound System and Method

Figure 1:
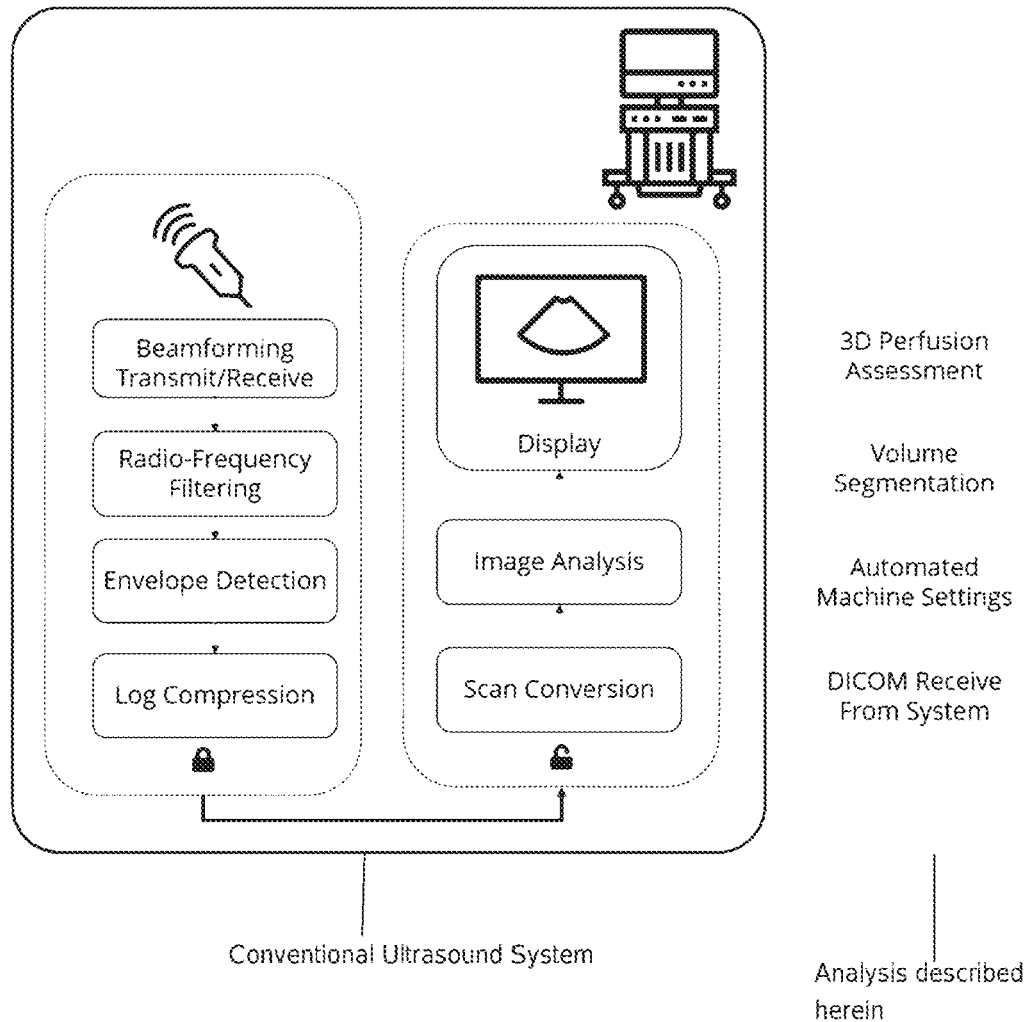
FIG. 1 is a schematic diagram of the analysis components of the methods and systems described herein for the automated, non-invasive measurement of perfusion using 3D power Doppler. It is envisaged that the components in orange may be incorporated into an ultrasound machine This method assumes no ability to be able to access data from a commercial system, however with access these modules slot between the steps that are not available to researchers (padlock closed) and those that are, including final display on the system itself.

FIG. 1 illustrates the additional analysis components for the automated, non-invasive measurement of perfusion using conventional power Doppler ultrasound. The conventional ultrasound machine (e.g., LOGIQ 9 (GE Healthcare, Milwaukee, Wis) or EPIQ 7G (Philips, Cambridge, Mass) with 4D3C-L (2-5 MHz) and X6-1 (1-6 MHz) transducers, respectively) contains both a display and a scanning head. The scanning head is movable or a 2D matrix of transducers that is to enable various regions of a subject to be imaged. The scanner emits ultrasound signals which are incident upon the scanning subject. Due to the variation of densities within the subject, or a volume of tissue within the subject, the incoming signals may become reflected signals, or echoes. The frequency differences between the incident signals and the echoes are analyzed by the ultrasound machine to create one or more images.

Within an image, a region of interest such as an organ or portion thereof may be designated. This region of interest may contain several types of hard tissues (i.e., tissues in which no blood flows) and tissues through which varying amounts of blood flow. The method provided herein invention provides a quantitative measure for the percentage of moving blood in a specific region of interest (ROI), i.e. the Fractional Moving Blood Volume (FMBV).

In one embodiment raw ultrasound three-dimensional or four-dimensional volumes are acquired on selection by the ultrasound operator by first selecting the region of interest. Typically the region of interest is an organ (e.g. a kidney) or a portion of an organ such as renal cortex or medulla).

The operator selects a 'mode' of display and analysis for '3D-FMBV' measurement and the ultrasound machine automatically selects predetermined optimized settings taken to enhance ultrasound images. For example, ultrasound image quality may be enhanced by adjusting such settings as wall motion filter, pulse repetition filter, clutter removal, overall gain, power Doppler gain, pulse repetition filter, line density, ensembling, power Doppler gain level, B-Mode gain compensation (TGC), lateral gain compensation (LGC), dynamic range, and frequency. In this regard, time gain compensation (TGC) may be applied to ultrasound images, to enhance image quality, by accounting for attenuation caused by tissues being imaged. By increasing received signal intensity with depth, artifacts may be reduced. Further, LGC can be used to enhance the image quality by adjusting gain setting as a function of lateral scan position.

The automatic selection of these settings is in contrast to current practice in which the operator is obliged to manually vary and select the correct setting based of their experience and visual cues from displayed images which introduces undesirable subjectivity and operator to operator variation.

With reference to FIG. 1, a typical ultrasound (US) system comprises, for example, a transmitter, an ultrasound probe, a transmit beamformer, a receiver, a receive beamformer, a RF processor, a RF/IQ buffer, a user input module, a signal processor, an image buffer, and a display system.

The transmitter may comprise suitable circuitry that may be operable to drive an ultrasound probe. The transmitter and the ultrasound probe may be implemented and/or configured for one dimensional (1 D), two dimensional (2D), three dimensional (3D) and/or four dimensional (4D) ultrasound scanning. The ultrasound probe will comprise a group of transmit transducer elements and a group of receive transducer elements, which may be the same elements. The transmitter may be driven by the transmit beamformer which comprises suitable circuitry such that is operable to control the transmitter. The transmitter, through a transmit sub-aperture beamformer emit ultrasonic transmit signals into a region of interest.

The group of transmit transducer elements can be activated to transmit ultrasonic signals. The ultrasonic signals may comprise, for example, pulse sequences that are fired repeatedly at a pulse repetition frequency (PRF), which may typically be in the kilohertz range. The pulse sequences may be focused at the same transmit focal position with the same transmit characteristics. A series of transmit firings focused at the same transmit focal position are referred to as a "packet." The transmitted ultrasonic signals may be back-scattered from structures in the object of interest, like tissue or fluid flowing through a tissue, to produce echoes. The echoes are received by the receive transducer elements.

The receive transducer elements in the ultrasound probe are operable to convert the received echoes into signals, beamforming by a beamformer and are then communicated to a receiver.

The receiver may be operable to receive and demodulate the signals from the probe transducer elements or beamformer. In some embodiments the receive beamformer may be operable to perform digital beamforming processing to, for example, output a beam summed signal. The resulting processed information may be converted back to corresponding RF signals. The corresponding output RF signals that are output from the receive beamformer may be communicated to an RF processor.

The RF processor is operable to demodulate the RF signals. This process is analogous to the demodulation of radio signals and is to remove the carrier signal and reconstruct the signal envelope (In FIG. 1, this is referred to as envelope detection). In one embodiment the RF processor comprises a demodulator that is operable to demodulate the RF signals to form In-phase and quadrature (IQ) data pairs (e.g., B-mode and color IQ data pairs) which are representative of the corresponding echo signals. The RF or IQ signal data may then be communicated to an RF/IQ buffer.

Typical ultrasound machines have a user input module operable to enable obtaining or providing input to the ultrasound system. For example, the user input module may be used to input patient data, surgical instrument data, scan parameters, settings, configuration parameters, change scan mode, and the like. In this regard, the user input module is operable to configure, manage and/or control operation of transmitter, the ultrasound probe, the transmit beamformer, the receiver, the receive beamformer, the RF processor, the RF/IQ buffer, the signal processor, the image buffer, and/or the display system.

The signal processor is operable to process the ultrasound scan data (e.g., the RF and/or IQ signal data) and/or to generate corresponding ultrasound images, for presentation on a display system. The signal processor is operable to perform one or more processing operations according to a plurality of selectable ultrasound modalities on the acquired ultrasound scan data. In some instances, the signal processor may be operable to perform compounding, motion tracking, and/or speckle tracking. Acquired ultrasound scan data may be processed in real-time during a scanning session as the color flow and B-mode echo signals are received. Additionally or alternatively, the ultrasound scan data may be stored temporarily in the RF/IQ buffer during a scanning session and processed in less than real-time in a live or off-line operation.

In operation, the ultrasound system is used to generate ultrasonic images, including two-dimensional (2D), three-dimensional (3D) and/or four-dimensional (4D) images. In this regard, the ultrasound system may be operable to continuously acquire ultrasound scan data at a particular frame rate, which may be suitable for the imaging situation in question. For example, frame rates may range from 20-70 but may be lower or higher. The acquired ultrasound scan data may be displayed on the display system at a display-rate that can be the same as the frame rate, or slower or faster. An image buffer is included for storing processed frames of acquired ultrasound scan data that are not scheduled to be displayed immediately. Preferably, the image buffer is of sufficient capacity to store at least several seconds' worth of frames of ultrasound scan data. The frames of ultrasound scan data are stored in a manner to facilitate retrieval thereof according to its order or time of acquisition.

In some instances, the ultrasound system is configured to support grayscale and color based operations. For example, the signal processor may be operable to perform grayscale B-mode processing and/or color processing. The grayscale B-mode processing may comprise processing B-mode RF signal data or IQ data pairs. For example, the grayscale B-mode processing may enable forming an envelope of the beam-summed receive signal by computing the quantity $(I2+Q2)^{1/2}$. The envelope can undergo additional B-mode processing, such as logarithmic compression to form the display data.

In a typical ultrasound machine the data is converted to X-Y format for video display. The scan-converted frames can be mapped to grayscale for display. The B-mode frames that are provided to the image buffer and/or the display system. The color processing may comprise processing color based RF signal data or IQ data pairs to form frames to overlay on B-mode frames that are provided to the image buffer and/or the display system. The grayscale and/or color processing may be adaptively adjusted based on user input e.g., a selection from the user input module, for example, for enhance of grayscale and/or color of particular area.

The ultrasound system may incorporate user controls for adjusting parameters relating to image quality, such as overall gain, power Doppler gain, pulse repetition filter, TGC, LGC, dynamic range, frequency, and the like. Users of the ultrasound system may then attempt to determine or identify optimum arrangement(s) of the user controls to achieve desired/optimal enhancement of the images. Reaching or determining these arrangements may require, however, significant interactions between the user and the ultrasound system. Such extensive interactions may be uncomfortable and/or time-consuming, and consequently users may forgo attempts to identify these optimum arrangements, and as a result images may not be as optimized often forcing users (or others using the images) to work with less optimal images. The level of user input required may lead to inaccuracies in the images or parameters calculated from the images, it also leads to greater inter-user variation.

In various implementations, the ultrasound system described herein is configured to receive the log compressed data, which may comply with the Digital Imaging and Communications in Medicine (DICOM) standard and to perform automatic image quality enhancement. For example, the ultrasound system may be configured to enable enhancing quality of ultrasound images and hence enabling more accurate segmentation by performing automatic adjustment of various parameters such as overall gain, power Doppler gain, pulse repetition filter, dynamic range, frequency, time gain compensation (TGC), lateral gain compensation (LGC), etc. In this regard, gain may be adjusted, typically after beamforming, with gain adjustments comprising, for example, TGC gain adjustments, which may be adjustments in the axial direction carried out by increasing or decreasing gain as a function of depth, and/or LGC gain adjustments, which may be adjustments to gain settings as function of lateral scan position.

In power Doppler imaging intensity information can skewed by under or over saturation due to unoptimized setting of the power Doppler gain value. High values can lead to a "bloom effect" where noise artefacts can corrupt vascular information. A low gain setting can lead to true vascular signal not being displayed due to the cutoff effect of the high-pass wall motion filter. An inappropriate selection of gain value is known to affect the quality of the power Doppler data obtained. To obtain best perfusion estimation, an appropriate gain value is required to be selected, that maximises appearance whilst minimising noise, which is termed the 'sub-noise' gain level.

Normally, the determination of the appropriate SNG level is dependent on human interpretation. It is limited by human errors, and not always reproducible. The technique to optimize PD gain setting to just at the level that artefactual noise is observed has been proposed manually but can be performed automatically.

This automated technique takes display PD data and compute a percentage presence of PD for a given region. Using a piecewise-linear regression technique, regressing this percentage amount of PD in a given region against a range of gain values that under, over and well saturates the appearance of PD.

By using a piece-wise linear regression technique with a defined number of three line segments fits the problem and the end point of the first segment/start of the second is determined as the point that best fits the sub-noise gain level.

Segmentation—Neural Network

Image segmentation, in which the region of interested is identified, is the key to subsequent processing and is a primary determinant of the accuracy of any analysis carried out in the segmented image data. In conventional clinical practice segmentation is generally performed by manual tracing, which is laborious, time-consuming, skill- and experience-dependent. Consequently, reliable and automatic segmentation methods, such as those described herein are preferred to segment the region of interest from the ultrasound image.

Figure 2:
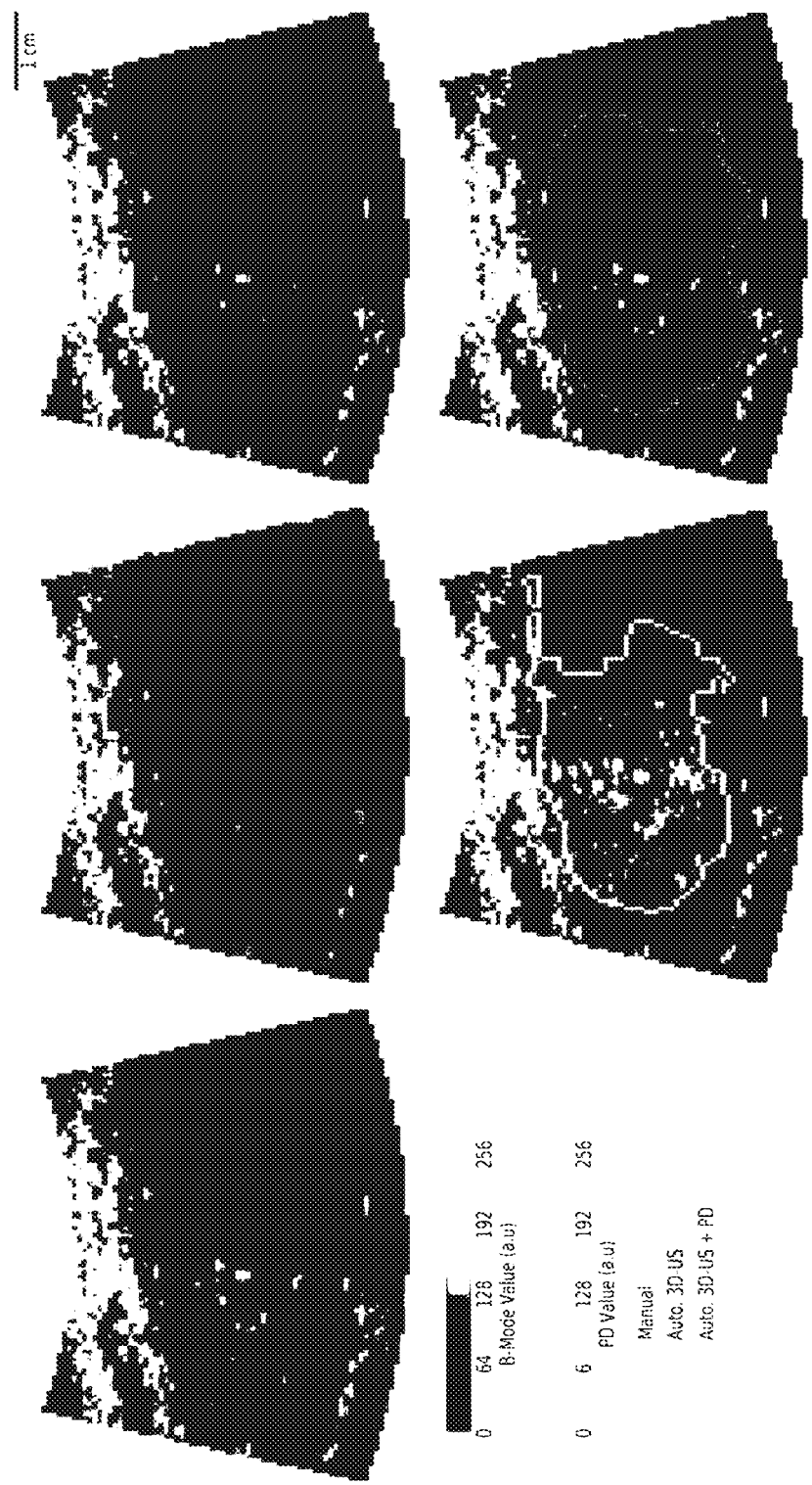
FIG. 2 illustrates a 2D slice from 3D-US of Fetal Kidney. Showing B-Mode (greyscale; top-left), power Doppler (orange; top-middle) with outline of manual labelling of the kidney (red; top-right), shown with only B-Mode US, with convolutional neural network (CNN) trained on 3D B-Mode data (blue; bottom-middle) and finally, with 3D-US and PD data as inputs to the CNN (green; bottom-right).
Figure 3:
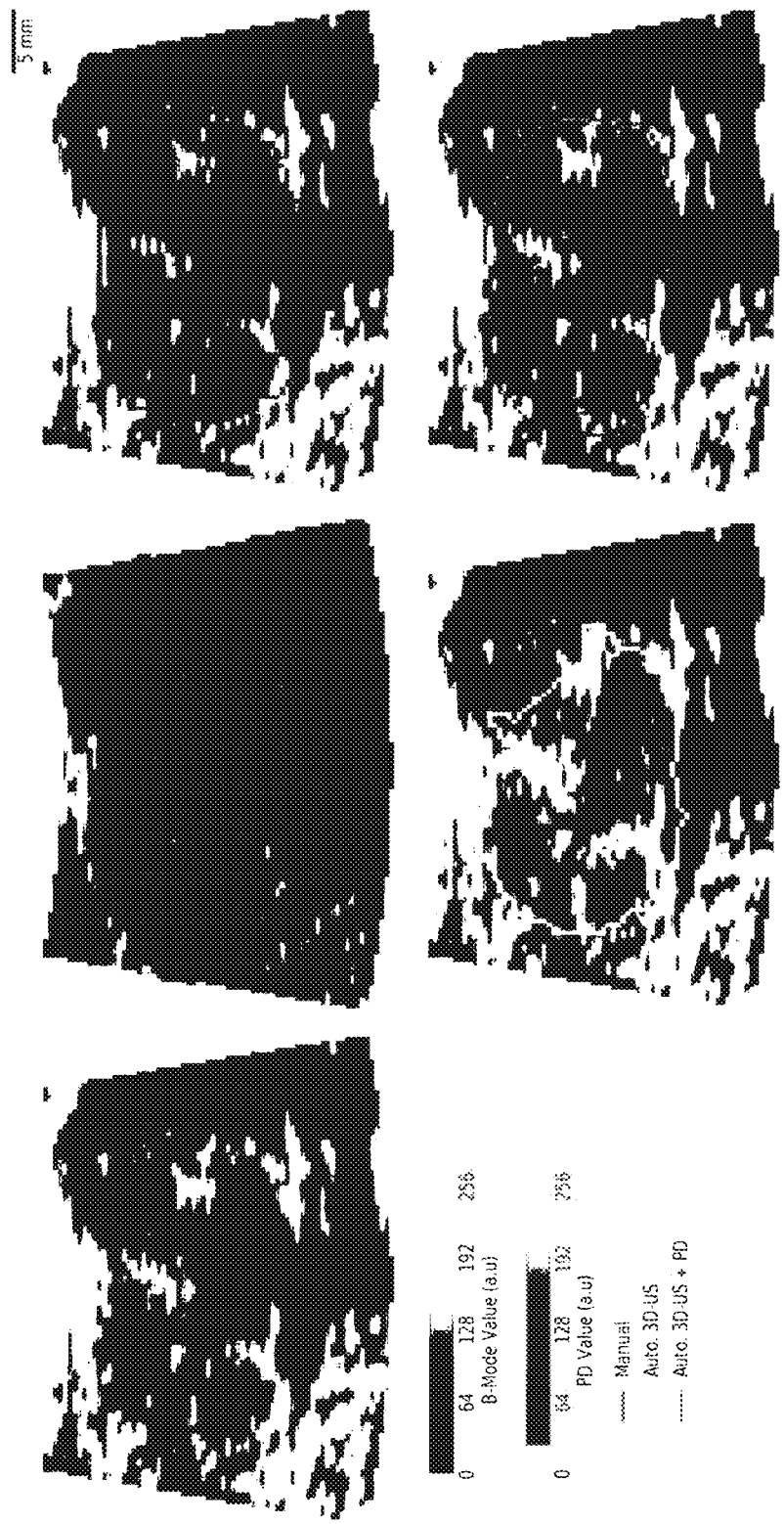
FIG. 3 illustrates another example of 2D slice from 3D-US of Fetal Kidney. Showing B-Mode (greyscale; top-left), power Doppler (orange; top-middle) with outline of manual labelling of the kidney (red; top-right), shown with only B-Mode US, with convolutional neural network (CNN)

With reference to FIGS. 2 and 3, in some embodiments the system utilizes a fully convolutional neural network (fCNN) for example using a dual-modality input fusion block that incorporates both 3D B-Mode and power Doppler (PD) volumes, in order to provide increased complementary features and improve segmentation accuracy.

Various fCNN neural networks may be used, for example U-Net, V-Net, and UNet++ are all suitable. These architectures are based on the 2D U-Net architecture, with being further modified to accommodate for the memory requirements of 3D segmentation. All models used a cross entropy loss function and optimized using Adam gradient descent $\beta 1=0:9$, $\beta 2=0:999$ and $\varepsilon=1\times 108$) with an initial learning rate of $10^3$. These models can be trained for 4 epochs or more with a batch size of 25 or more.

U-Net is a 3D fCNN that was used to segment the placenta from 3D-ultrasound volumes. To accommodate for the processing power required for 3D segmentation, modifications are made to the number of layers and channels in contrast to the original U-Net architecture. The max pooling operations were also replaced with strided convolutions to further decrease the GPU memory requirements. The model can be trained with, for example input patches of size 78×78×78 voxels extracted from the full volume.

The V-Net is another 3D modification to the U-Net architecture with greater emphasis placed on volumetric medical image segmentation. In contrast to U-Net, the V-Net utilizes varying number of convolution blocks at each stage (one to three convolution blocks) as well as volumetric kernels of size 5×5×5 voxels. However, due to memory constraints, this can be reduced to kernels of size 3×3×3 voxels. Similar to the U-Net, down convolutions are handled using strides of two and the skip connections (element-wise sum operations) between layers bring back the spatial data that was lost during the down convolutions. The model can be trained with input patches of size 64×64×64 voxels extracted from the full volume.

UNet++ is an adaptation of the 2D U-Net with redesigned skip connections that aims to reduce the semantic gap between the feature maps from the encoding and decoding paths. It utilizes a dense convolution block which consists of varying number of convolution layers depending on the network level (i.e. more convolutions in the higher levels). The layers are fused together through concatenation in an attempt to provide an easier optimization problem for the network. These convolution blocks replace the previously used element-wise sum operations when merging information between the encoding and decoding paths. Similar to the V-Net, the model can be trained with input patches of size 64×64×64 voxels extracted from the full volume.

Accordingly, segmentation accuracy can be optimized by incorporating means for the fCNN described above. Further, the ultrasound system may be configured to display the optimization outcome. Accordingly, the ultrasound system may not only be operable to automatically optimize various settings, but may also be operable to provide feedback to a an operator, particularly with respect to settings of user control that correspond to optimal corrections. This may also allow operators to apply the same settings in future, such as when performing ultrasound imaging on the same patients and/or organs.

For example, in various embodiments of the invention, the ultrasound system may be configured to support automatic gain compensation (e.g., TGC and/or LGC) correction/optimization, and to support providing feedback to users relating to user controls arrangements for achieving optimal TGC in the systems.

Data Partitioning

Once a 3D volume is scanned the partitioning process enables each structural element or voxel to be labelled with their distance to a reference point (e.g. the transducer head) which can be automatically performed, e.g. by a program or script. The program or script reads the radius data (r) and the scan-line axial resolution from the backward transformed toroidal space data, or the raw toroidal space data.

As an option the program is adapted to visually label the portions of the volumes, i.e. the voxels so that their depths or distances from the transducer head can be discerned on the display. For example this can involve coloring or shading. When the labelled toroidal space data is forward transformed into the display space, the displayed data will now convey information relating to the positions of the labelled portions in terms of their distances from the transducer head (e.g. see FIG. 5).

Once labelled the volumes can be partitioned into a set of regions wherein each region is geometrically the same distance from the transducer as another within a set bound based on setup or the axial resolution of the system or any other limit that avoids sub-sampling or the impact of attenuation if too shallow or deep a region, respectively.

Attenuation is a non-linear effect, impacting on the power Doppler intensity values meaning that for an organ, 2-3 cm in depth attenuation will have varying impact on intensity values despite the same underlying bloodflow. The region is partitioned to overcome and compensate for this difference in depth.

In one embodiment a sweep transducer is used in which data is acquired in a toroidal space based on angles on the B-Mode and volume angle (θ, φ) to display into x,y,z Cartesian space. This process is known as scan conversion wherein individual scanlines and their point set are converted into a regular Cartesian grid.

Forward Transformation

The raw data, which is expressed in the toroidal space (θ, φ, r), is transformed to the Cartesian (x, y, z). One method for this transformation uses the following equations:

$$x=r\times\sin(\theta)$$

$$y=-\sin(\phi)\times(r\cos(\theta)-d)$$

$$z=d\times(1-\cos(\phi))+r\times\cos(\theta)\times\cos(\phi)$$

where:
- θ is the angle in the B-Mode 2D image (shown as +/−37.5 or a 75 degree sweep in FIG. 4A)
- φ is the angle each single B-Mode is swept through (this is in the y-plane; not seen in FIG. 4A)
- r is the distance from the B-Mode focus (i.e. the distance from the scan-head to the first image sample)
- d is the distance between 2D sweeps (i.e. the size of the step the scan-head takes between each 2D acquisition)

Backward Transformation

Following the forward transformation or scan-conversion into the "display" space, the annotation of a volume of interest (V01) occurs. The annotation is either user defined or calculated by the FCNN or other image analysis method. This annotation is visible in FIG. 4 and FIG. 5, as an outline defining the organ mask for the kidney. Whereas human annotation of the ROI is typically done in the "display space", algorithms for image masking allow annotation to be performed in either the display space or in the toroidal space.

The present technology performs "post-processing" on the forward transformed data, by performing a 'backward' transform. The backward transform, from the display space back to the toroidal or scan line space, can be performed using the inverse of the equations described above.

The backward transformation is able to determine, for any labelled pixel or voxel in the display space, its distance along a particular scan-line, i.e., its distance from the transducer head.

The backward transformation is performed for a set co-ordinates in the x,y,z (Cartesian) space, to convert them back into the toroidal space (r, θ, ϕ). One method of backward transformation uses the following equations:

$$r = \sqrt{x^2 + \left(d - \frac{y}{\sin(\phi)}\right)}$$

$$\phi = -\tan^{-1}\left(\frac{y}{z-d}\right)$$

$$\theta = \sin^{-1}\left(\frac{x}{b}\right)$$

Where r, d, θ, ϕ are above.

Using the aforementioned steps, the scan data is converted into the display (Cartesian) space, annotated and then converted back into the scan-line (Toroidal) space.

The distance from the transducer (r) and the axial resolution down the scan-line are known. Therefore, the distance of each labelled pixel in the original image can be calculated. Finally, the labelled pixels (voxels shown in 2D) in the toroidal space can then be forward transformed using the initial process for human display.

The advantage of performing the backward transform, and labelling the "slices" in the toroidal space, before forward transforming the partitioned data back to the display space, is that the positions of the voxels or pixels in the display space can be given a context, in terms of their distance from the transducer head. Thus, the effect of attenuation of the ultrasound by the tissue, and the effect of the pixel or voxel's relative position to other sample areas (i.e. pixels or voxels) in the region of interest, can be investigated.

Fractional Moving Blood Volume

The imaging data for each segment or partition of each segment is used to calculate the FMBV, more specifically a series of 2D segments are used to calculate the 3D-FMBV. Within each segment a percentage of the perfusion measure in relation to a maximum (100%) value, is calculated for each voxel. An interim value is then determined from the percentages of the individual voxels. The interim value is a representative value of the FMBV measurements for the voxels within the segment. Various methods for taking the representative value from the FMBV measurements can be used, as can be chosen from statistical methods which suit the circumstance. For instance, the representative value may simply be a mean or a median value of the FMBV measurements for the voxels in the segment.

Accordingly the 3D-FMBV analysis algorithm can be summarised by the following steps
 (a) identifying, in a reference portion of each partition, a reference Doppler power level associated with 100% flow;
 (b) computing a mean power estimate equal to the sum of respective target Doppler power levels of a plurality voxels within the partition divided by the number of the plurality voxels within the partition;
 (c) computing, for each partition, a fractional moving blood volume estimate by normalizing the mean power to the reference Doppler power level; and
 (d) ensembling the fractional moving blood volume estimates to determine the 3D-FMBV for the organ, tissue or region thereof.

In another embodiment a single region is used where a small geometric region is assessed.

A set of sub regions labelled by millimetre distance from the transducer head upon which an FMBV measurement can also be performed, for example in the scan space where data is partitioned based on distance r from the transducer. Taking an fCNN output in the display space, this is inverse transformed into the scan space, then a forward transform is performed to generate a distance map based on the distances provided in the scan space but not available in the display.

For each set of volume or image elements within a single region a classical FMBV calculation is performed as per the algorithm laid out in Rubin et al Radiology Radiology. 1997 December; 205(3):757-65, which is incorporated herein by reference in its entirety:

This algorithm computes a cumulative Doppler power distribution function is calculated for the set number of Power Doppler values within the region of interest.

A point of inflexion of the 'knee' of the distribution is then computed in two methods. A best-fit line for the cPDF is fitted and the intersection of two tangents plotted from the intersection of best fit line to the cPDF is used. A second method uses the best-fit line and rotates the cPDF to the abscissa and the global maximum is used. The knee is then selected using either of these methods and for all intensity values above this position are given a value of 100% blood and those below normalised to this value. From this, a mean FMBV is calculated for this region.

For an image where multiple FMBV values are calculated an overall representative value based on multiple regions is computed. The overall representative value can be calculated any method known in the art, and the specific method chosen. For example, the value can be calculated by taking an average or a median of the representative measures.

In embodiment where a 4D acquisition was performed, 3D-FMBV can be calculated for each phase of the cardiac cycle. The value for 3D-FMBV and 4D vascular impedance for that region would be displayed either on the host US system or external display Some segments may not have enough voxels (data points) to provide a reliable estimate of FMBV. These segments are discarded, for example segments having fewer than 400 voxels are discarded.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

What is claimed is:

1. A method of quantifying a 3D fractional moving blood volume (3D-FMBV) in a tissue volume of a subject, comprising:
 (a) acquiring, by a processor, images of the tissue volume from a power Doppler scan of the tissue volume;
 (b) applying by the processor, image enhancement settings to the images to produce image data;
 (c) segmenting, by the processor, an organ, tissue or region thereof from the image data;

(d) determining, by the processor, geometric partitions of the segments in a toroidal space based on a distance from a transducer head of an ultrasound system; and (e) computing, by the processor, a 3D-FMBV from the geometric partitions using a 3D-FMBV analysis algorithm.

2. The method of claim 1, wherein the segmenting uses a neural network trained to identify an organ or tissue.

3. The method of claim 1, wherein the segmenting of the image data is performed in Cartesian space, and the image data is transformed from the Cartesian space to the toroidal space before determining the geometric partitions.

4. The method of claim 1, wherein the image enhancement settings are selected from wall motion, overall gain, power Doppler gain, pulse repetition filter, line density, gain compensation, lateral gain compensation, dynamic range, frequency, and any combination thereof.

5. The method of claim 1, wherein the image enhancement settings are automatically applied to the images.

6. The method of claim 2, wherein the neural network is trained on a combination of power Doppler and greyscale imaging.

7. The method of claim 6, wherein the neural network is a fully convolutional neural network.

8. The method of claim 1, wherein both the segmenting of the image data and the determining of the geometric partitions are performed in the toroidal space, and the method further comprises transforming the image data to the Cartesian space and displaying the 3D-FMBV in the Cartesian space.

9. The method of claim 2, wherein, the 3D-FMBV analysis algorithm comprises:
   (a) identifying, in a reference portion of each partition, a reference Doppler power level associated with 100% flow;
   (b) computing a mean power estimate equal to the sum of respective target Doppler power levels of a plurality voxels within the partition divided by the number of the plurality voxels within the partition;
   (c) computing, for each partition, a fractional moving blood volume estimate by normalizing the mean power to the reference Doppler power level; and
   (d) ensembling the fractional moving blood volume estimates to determine the 3D-FMBV for the organ, tissue or region thereof.

10. The method of claim 1, wherein the images are acquired in synchronisation with the cardiac cycle of the subject.

11. The method of claim 10, wherein images that represent a particular phase of the cardiac cycle are selected.

12. The method of claim 11, wherein a 4D-FMBV is computed using the 3D-FMBV analysis algorithm for each of the selected images.

13. The method of claim 1, further comprising generating a visual display of the 3D-FMBV or the 4D-FMBV.

14. An ultrasound system comprising a processor adapted to receive log compression data from a signal processor, and a non-transitory machine readable storage medium storing instructions which are executable by the processor to:
   (a) acquire images of a tissue volume from a power Doppler scan of the tissue volume;
   (b) apply image enhancement settings to the images to produce image data;
   (c) segment an organ, tissue or region thereof from the image data;
   (d) determine geometric partitions of the segments in a toroidal space based on distance from a transducer head of the ultrasound system; and
   (e) compute a 3D-FMBV from the partitions using a 3D-FMBV analysis algorithm.

15. The ultrasound system of claim 14, wherein the segmenting of the image data is performed in Cartesian space and the image data is transformed from the Cartesian space to the toroidal space before determining the geometric partitions.

16. The ultrasound system of claim 14, wherein the image enhancement settings are selected from wall motion, overall gain, power Doppler gain, pulse repetition filter, line density, gain compensation, lateral gain compensation, dynamic range, frequency, and any combination thereof.

17. The ultrasound system of claim 14, wherein the 3D-FMBV analysis algorithm comprises:
   (a) identifying, in a reference portion of each partition, a reference Doppler power level associated with 100% flow;
   (b) computing a mean power estimate equal to the sum of respective target Doppler power levels of a plurality voxels within the partition divided by the number of the plurality voxels within the partition;
   (c) computing, for each partition, a fractional moving blood volume estimate by normalizing the mean power to the reference Doppler power level; and
   (d) ensembling the fractional moving blood volume estimates to determine the 3D-FMBV for the organ, tissue or region thereof.

18. A non-transitory machine readable storage medium comprising instructions executable by a processor to:
   (a) acquire images of a tissue volume from a power Doppler scan of the tissue volume;
   (b) apply image enhancement settings to the images to produce image data;
   (c) segment an organ, tissue or region thereof from the image data;
   (d) determine geometric partitions of the segments in a toroidal space based on distance from a transducer head of an ultrasound system; and
   (e) compute a 3D-FMBV from the partitions using a 3D-FMBV analysis algorithm.

19. The non-transitory machine readable storage medium of claim 18, wherein the segmenting of the image data is performed in Cartesian space and the image data is transformed from the Cartesian space to the toroidal space before determining the geometric partitions.

20. The non-transitory machine readable storage medium of claim 18, wherein the 3D-FMBV analysis algorithm comprises:
   (a) identifying, in a reference portion of each partition, a reference Doppler power level associated with 100% flow;
   (b) computing a mean power estimate equal to the sum of respective target Doppler power levels of a plurality voxels within the partition divided by the number of the plurality voxels within the partition;
   (c) computing, for each partition, a fractional moving blood volume estimate by normalizing the mean power to the reference Doppler power level; and
   (d) ensembling the fractional moving blood volume estimates to determine the 3D-FMBV for the organ, tissue or region thereof.

* * * * *